United States Patent [19]

Schaumberg et al.

[11] Patent Number: 4,713,372

[45] Date of Patent: Dec. 15, 1987

[54] 2-CHLOROPENTOSTATIN COMPOUND HAVING ADENOSINE DIAMINASE INHIBITORY ACTIVITY

[75] Inventors: John P. Schaumberg, Ypsilanti; Gerard C. Hokanson; James C. French, both of Ann Arbor; Josefino B. Tunac, Troy; Marjorie A. Underhill, Pigeon, all of Mich.

[73] Assignee: Warner-Lambert Company, Morris Plains, N.J.

[21] Appl. No.: 796,139

[22] Filed: Nov. 8, 1985

Related U.S. Application Data

[63] Continuation of Ser. No. 590,239, Mar. 16, 1984, abandoned.

[51] Int. Cl.[4] .................... A61K 31/70; C07H 17/02
[52] U.S. Cl. .................................... 514/45; 536/24
[58] Field of Search ................. 536/24, 26; 514/46, 514/45

[56] References Cited

U.S. PATENT DOCUMENTS

| | | | |
|---|---|---|---|
| 3,923,785 | 12/1975 | Ryder et al. | 260/211.5 R |
| 3,959,257 | 5/1976 | Umezawa et al. | 260/211.5 R |
| 4,145,531 | 3/1979 | Eckstein et al. | 536/26 |
| 4,163,839 | 8/1979 | Umezawa et al. | 536/24 |
| 4,195,176 | 3/1980 | Baker et al. | 536/24 |

OTHER PUBLICATIONS

Jackson et al., Advances in Enzyme Regulation, 25, 125–139 (1986).

Verheyden et al., Halo Sugar Nucleosides III, Reactions for the Chlorination and Bromination of Nucleoside Hydroxyl Groups, J. Org. Chem. 37(14), 2289–2299 (1972).

*Primary Examiner*—Nicky Chan
*Attorney, Agent, or Firm*—Jerry F. Janssen

[57] ABSTRACT

2'-Chloropentostatin is a potent inhibitor of the enzyme adenosine deaminase and possesses utility as an agent for potentiating the activity of antiviral agents for the treatment of DNA viruses which agents contain an adenine moiety, such as 9-(beta-D-arabinosyl)adenine. A pure strain of actinomycete, designated ATCC 39365 which is capable of producing 2'-chloropentostatin, a method of producing 2'-chloropentostatin by aerobic fermentation, and pharmaceutical compositions including 2'-chloropentostatin are also disclosed.

3 Claims, 3 Drawing Figures

2-CHLOROPENTOSTATIN COMPOUND HAVING ADENOSINE DIAMINASE INHIBITORY ACTIVITY

This is a continuation of application Ser. No. 590,239 filed Mar. 16, 1984, abandoned.

BACKGROUND OF THE INVENTION

The efficacy of a number of adenine nucleosides which act as both antitumor and antiviral agents is severely limited due to their rapid deactivation in vivo by the action of adenosine deaminase, an enzyme present in most mammalian body tissues. The compounds (R)-3-(2-deoxy-beta-D-erythropentofuranosyl)-3,6,7,8-tetrahydroimidazo[4,5-d][1,3]diazepin-8-ol (commonly known as pentostatin), disclosed in U.S. Pat. No. 3,923,785, and its ribo-analog, (R) -3-(beta-D-ribofuranosyl)-3,6,7,8-tetrahydroimidazo[4,5-d][1,3]diazepin-8-ol (commonly known as coformycin), disclosed in Japanese Pat. No. 875,639 and U.S. Pat. No. 4,151,347, are potent inhibitors of adenosine deaminase.

SUMMARY OF THE INVENTION

2'-Chloropentostatin is a novel analog of pentostatin which is produced by an isolate of an actinomycete designated ATCC 39365.

In accordance with one aspect of the present invention, there is provided a compound having structural formula I

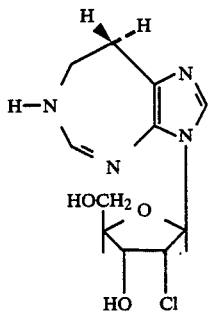

and the name (R)-3-(2-chloro-2deoxy-beta-D-ribofuranosyl)-3,6,7,8-tetrahydroimidazo[4,5-d][1,3]diazepin-8-ol and its pharmaceutically acceptable acid addition salts, which compound possesses potent adenosine deaminase inhibitory activity. The name 2'-chloropentostatin will be used throughout this specification to refer to the compound.

In another aspect, the present invention provides a pure strain of the 2'-chloropentostatin-producing microorganism having the identifying characteristics of isolate ATCC 39365.

In accordance with another aspect, the present invention provides a method of producing 2'-chloropentostatin by cultivating the isolate of actinomycete identified as ATCC 39365 under aerobic conditions in a medium containing assimilable sources of carbon and nitrogen until a substantial quantity of 2'-chloropentostatin is produced, and subsequently isolating the compound.

In another aspect of the present invention, there are provided pharmaceutical compositions useful for the treatment of DNA viruses comprising an effective amount of 2'-chloropentostatin or one or more of its pharmaceutically acceptable acid addition salts together with an effective amount of an antiviral agent which contains an adenine moiety such as 9-(beta-D-arabinofuranosyl)adenine and a pharmaceutically acceptable carrier.

In a further aspect, the present invention provides a method of treating DNA viruses in a mammal comprising administering to a mammal in need of such treatment, an effective amount of 2'-chloropentostatin or a pharmaceutically acceptable salt thereof in combination with an effective amount of 9-(beta-D-arabinofuranosyl)adenine together with a pharmaceutically acceptable carrier.

DETAILED DESCRIPTION

Figure 1:
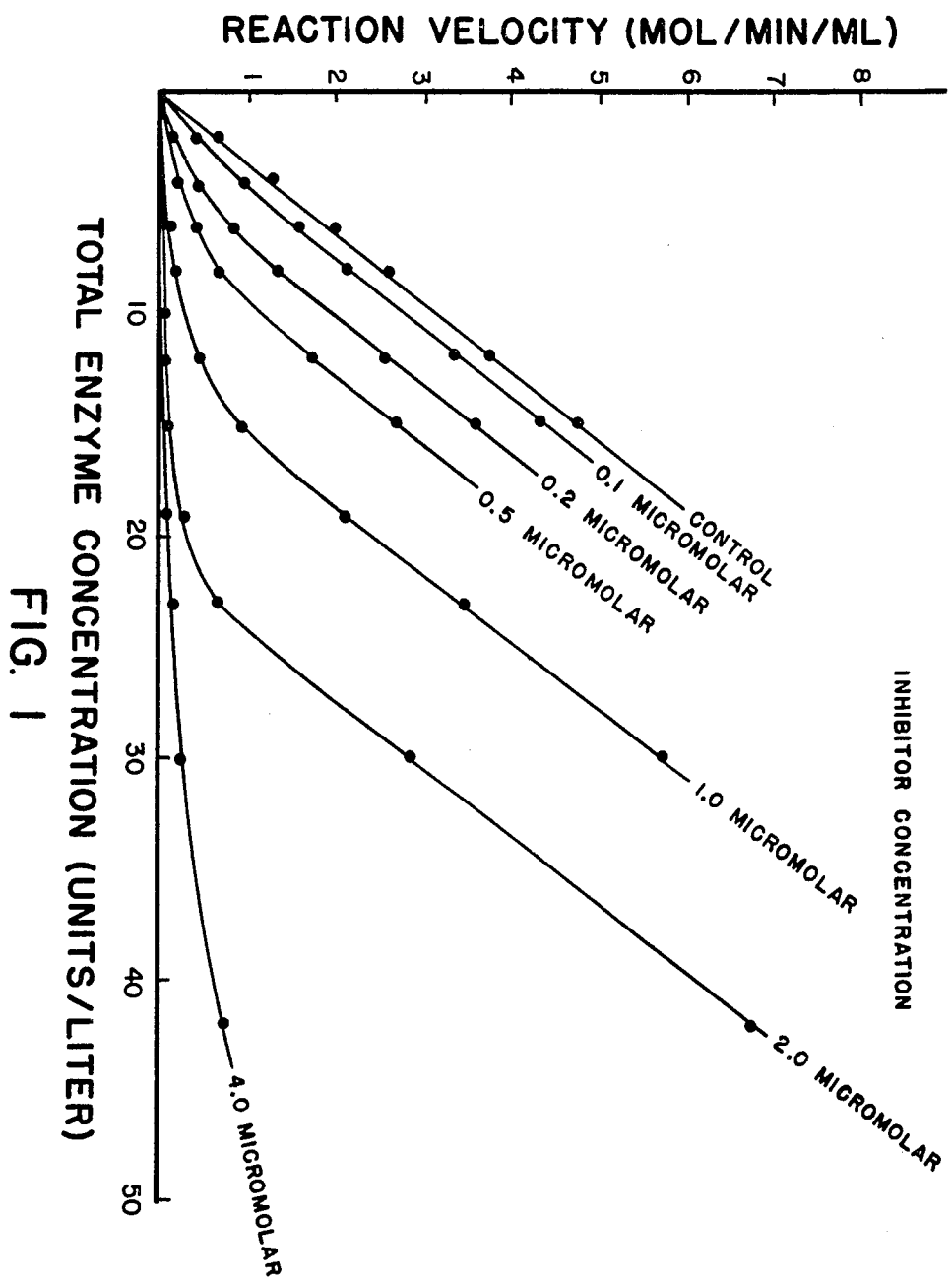
FIG. 1 is an Ackerman-Potter plot of the adenosine deaminase inhibitory action of 2'-chloropentostatin.

In accordance with the present invention, the compound 2'-chloropentostatin is produced by cultivating a selected isolate of actinomycete, designated ATCC 39365, until a substantial amount of 2'-chloropentostatin is formed, and subsequently isolating the compound.

The strain of actinomycete suitable for the purposes of this invention was found in a soil sample collected from North Carolina, USA. This microorganism was isolated from the soil sample using a suitable agar plating medium, one containing salts such as potassium phosphate, magnesium sulfate, and ferrous sulfate, and carbon sources such as glycerol and asparagine. The soil sample was plated onto the agar medium and incubated at a favorable temperature, particularly 45° C., to allow the development of the soil microorganisms.

The 2'-chloropentostatin-producing microorganism that was isolated from the agar plating medium is an as yet unidentified isolate of actinomycete and has been deposited with the American Type Culture Collection, Rockville, Md. 20852, where it is being maintained in their permanent collection as ATCC 39365. This organism, which produces 2'-chloropentostatin, is also being maintained as a dormant culture in lyophile tubes, cryogenic vials, and in soil tubes in the Warner-Lambert-/Parke-Davis Culture Collection, 2800 Plymouth Road, Ann Arbor, Mich. 48105, where it is designated as culture WP-886.

The compound 2'-chloropentostatin, which exhibits potent activity as an inhibitor of adenosine deaminase, is produced by isolate ATCC 39365 during aerobic fermentation under controlled conditions. The fermentation medium consists of sources of carbon, nitrogen, minerals, and growth factors. Examples of suitable carbon sources include glycerol and various simple sugars such as glucose, mannose, fructose, xylose, ribose, or other carbohydrate-containing compounds such as dextrin, starch, corn meal, and whey. The normal quantity of carbon source materials in the fermentation medium varies from about 0.1 to about 10 weight percent.

Nitrogen sources in the fermentation medium are inorganic, organic, and mixed inorganic-organic nitrogenous materials. Examples of such materials are cottonseed meals, soybean meal, corn germ flour, corn steep liquor, distiller's dried solubles, peanut meal, peptonized milk, and various ammonium salts.

The addition of minerals and growth factors to the fermentation medium is also helpful in the production of 2'-chloropentostatin. Examples of such mineral additives include sodium chloride, potassium chloride, ferrous sulfate, calcium carbonate, cobalt chloride, and zinc sulfate. Sources of growth factors include various yeast and milk products.

The preferred method of producing 2'-chloropentostatin is by submerged culture fermentation. According to this method, the fermentation medium ingredients are prepared in solution or suspension in water, and the mixture is subsequently sterilized by autoclaving or steam heating. The mixture is cooled following sterilization to a temperature between about 16° C. and 45° C. and the pH is adjusted to preferably between about pH 4 and about pH 8. The cooled, sterile medium is inoculated with the organism and thereafter fermentation is carried out with aeration and agitation.

In the submerged culture method, fermentation is carried out in shake-flasks or in stationary tank fermentors. In shake-flasks, aeration is effected by agitating the flask and contents to bring about contact of the medium with air. In stationary tank fermentors, agitation is provided by impellers which may take the form of disc turbines, vaned discs, open turbine or marine propellers. Aeration is accomplished by sparging air or oxygen into the agitated mixture. Adequate production of 2'-chloropentostatin is achieved under these conditions after a period of about two to ten days.

Alternatively, 2'-chloropentostatin may be produced by solid state fermentation of the microorganism.

The following examples are provided to illustrate the fermentative production of 2'-chloropentostatin. The examples are merely illustrative and are not to be read as limiting the scope of the invention as it is defined by the appended claims.

Fermentative Production of 2'-Chloropentostatin Shake-Flask Fermentation

EXAMPLE 1

The ATTCC 39365 culture, following its isolation by the agar plating technique, was transferred from its dormant state to an agar slant tube containing CIM 23 agar medium and incubated at 28° C. for 7–14 days. A portion of the microbial growth which developed in this slant tube was used to inoculate 5 ml of SD-05 seed medium contained in a 18×150 mm tube. The tube contents were shaken on a gyratory shaker at 170 rpm and incubated at 33° C. for four days.

TABLE 1

| Formulation of CIM 23 Agar Medium | |
|---|---|
| Amidex corn starch | 10 g |
| N—Z Amine, Type A | 2 g |
| Beef extract (Difco) | 1 g |
| Yeast extract (Difco) | 1 g |
| Cobaltous chloride 5H$_2$O | 20 mg |
| Agar | 20 g |
| Distilled Water | 1000 ml |

TABLE 2

| Formulation of SD-05 Seed Medium | |
|---|---|
| Amberex 1003 (Amberex Laboratories) | 5 g |
| Glucose monohydrate | 1 g |
| Dextrin-Amidex B411 (Corn Products) | 24 g |
| N—Z Case (Humko Sheffield) | 5 g |
| Spray-dried meat solubles (Daylin) | 3 g |
| Calcium carbonate | 2 g |
| Water | 1000 ml |

EXAMPLE 2

A 1.0-ml portion of the contents of the seed tube from Example 1 was transferred to a 300-ml shake-flask containing 50 ml of SM-31 screening medium. The inoculated flask contents were incubated at 33° C. for four days with shaking (170 rpm gyratory shaking, 5 cm throw).

TABLE 3

| Formulation of SM-31 Screening Medium | |
|---|---|
| Glucose monohydrate | 15 g |
| Lactose | 10 g |
| Distiller's solubles | 6.5 g |
| Peptonized milk | 3.5 g |
| Torula yeast | 2.5 g |
| Water, pH adjusted to 7.0 | 1000 ml |

To confirm the fermentation activity of the microorganism, a second microbial seed was prepared as described in Example 2 above and 2 ml of this seed was used to inoculate 50 ml of SM-31 screening medium contained in a 300-ml shake-flask. The inoculated flask was incubated at 300° C. for four days with shaking (170 rpm gyratory shaking, 5 cm throw).

EXAMPLE 3

The production of 2'-chloropentostatin in the fermentation beer of Example 2 was monitored by screening the beer against the microorganism *Streptococcus faecalis* 05045. Agar plates containing AM-10 assay medium were inoculated with this microorganism and paper discs (12.7 mm diameter), impregnated with the fermentation beer, were placed on the inoculated agar medium and incubated overnight at 37° C. The diameter of the zones of inhibition around each disc were measured. The size of the zone correlated with the amount of 2'-chloropentostatin present in the fermentation beer. The results of these measurements appear in Table 5.

TABLE 4

| Formulation of AM-10 Assay Medium | |
|---|---|
| K$_2$HPO$_4$ | 3.9 g |
| Dextrose | 25.0 g |
| Sodium citrate.2 H$_2$O | 34.4 g |
| Casein hydrolysate | 6.2 g |
| Asparagine | 375 mg |
| L-tryptophan | 125 mg |
| Cysteine | 312.5 mg |
| Glutathione | 0.31 mg |
| Thiamine HCl | 250 μg |
| Riboflavin | 625 μg |
| Ca pantothenate | 500 μg |
| Nicotinic acid | 500 μg |
| p-aminobenzoic acid | 625 μg |
| Biotin | 12.5 μg |
| Folic acid | 500 μg |
| Pyridoxine HCl | 2.5 mg |
| NaCl | 12.5 mg |
| MgSO$_4$ | 250 mg |
| FeSO$_4$ | 12.5 mg |
| MnSO$_4$.H$_2$O | 125.0 mg |
| Tween 80 | 62.5 mg |
| Adenine sulfate | 6.25 mg |
| Agar | 15.0 g |

TABLE 4-continued

| Formulation of AM-10 Assay Medium | |
|---|---|
| Water | 1000 ml |

TABLE 5

Initial Activity of Shake-Flask Fermentation Beers vs. *Streptococcus faecalis* 05045

| Fermentation Stage | Activity (zone diameter, mm) |
|---|---|
| Shake-flask I | 48 |
| Shake-flask II | 54 |

The crude fermentation beer also demonstrated antimicrobial activity against the microorganisms *Branhamella catarrhalis* 03596 and *Escherichia coli* 05117.

Large Batch Fermentation

EXAMPLE 4

A cryogenically preserved culture sample of ATCC 39365 was thawed and used to inoculate 600 ml of SD-05 seed medium contained in a 2-liter baffled Erlenmeyer flask. The flask and contents were incubated for 70 hours at 33° C. with shaking (130 rpm, 5 cm throw).

The contents of this shake-flask were used to inoculate 16 liters of SD-05 seed medium contained in a 30-liter stirred-jar fermentor. The jar contents were incubated at 33° C. for 24 hours with stirring at 300 rpm. During the incubation period, the jar contents were sparged with air at a rate of 1 volume air/volume medium/minute.

EXAMPLE 5

The contents of the stirred-jar of Example 4 were used to inoculate 160 gallons (605.7 liters) of SM-31 fermentation medium contained in a 200 gallon (757.1 liter) fermentation tank. The fermentation medium was sterilized by steam heating for 40 minutes at 121° C. and then cooled to 33° C. The cooled fermentation medium was inoculated with about 15 liters of the seed from Example 4 and allowed to ferment for five days at 33° C. with stirring at 155 rpm. The stirred tank contents were sparged with air at a rate of about 1 volume air/volume medium/minute during the fermentation. Antifoam P-2000 was used to control foaming as needed.

The production of 2'-chloropentostatin was monitored throughout the process by the assay described in detail above in Example 3 and the pH and percent growth, measured as sedimentation values, were recorded. The results of these tests appear in Table 6.

TABLE 6

| Fermentation time (hrs) | pH | % Growth (sedimentation values) | Zone Diameter (mm) |
|---|---|---|---|
| 0 | 5.95 | — | — |
| 12 | 6.2 | 4.0 | — |
| 24 | 6.7 | 5.3 | — |
| 36 | 7.3 | 10.0 | — |
| 48 | 7.0 | 11.3 | — |
| 71 | 7.0 | 16.7 | — |
| 96 | 6.9 | 18.7 | — |
| 119 | 6.85 | 20.7 | 48 |

EXAMPLE 6

A cryogenically preserved 1-ml sample of culture ATCC 39365 was thawed and aseptically transferred to a 2-liter baffled Erlenmeyer flask containing 600 ml of sterile SD-05 seed medium. The inoculated flask contents were incubated at 33° C. for 71 hours with shaking (130 rpm, 5 cm throw).

After 71 hours, the contents of the flask were aseptically transferred to 16 liters of sterile SD-05 seed medium contained in a 30-liter stirred-jar fermentor. This inoculum was incubated at 33° C. for 22 hours with stirring at 300 rpm and sparging with air at a rate of 1 volume air/volume medium/minute.

EXAMPLE 7

SM-19 medium (300 gallon, 1135.6 liters), contained in a 500-gallon (1892.7 liter) fermentation tank were sterilized by heating with steam at 121° C. for 40 minutes. The medium was cooled to 33° C. and then inoculated with 30 liters of inoculum prepared as described in Example 6. The inoculated medium was allowed to ferment for five days at 33° C. with stirring at 84 rpm and sparging with air at a rate of 0.375 volume air/volume median/minute. Dow-Corning "C" antifoam agent was used to control foaming as needed.

TABLE 7

| Formulation of SM-19 Fermentation Medium | |
|---|---|
| Dextrin | 1.5% |
| Lactose | 1.0% |
| Distiller's solubles | 0.65% |
| Peptonized milk | 0.35% |
| Torula yeast | 0.25% |
| Tap water | 100.0% |
| pH adjusted to 7.0 with NaOH | |

The production of 2'-chloropentostatin was monitored throughout the fermentation cycle using *Streptococcus faecalis* 05045 as described in Example 3. Additional fermentation parameters such as pH and percent sedimentation were also recorded. The results of these observations appear in Table 8.

TABLE 8

Fermentation in a 500-Gallon (1892.7 liters) Tank

| Fermentation time (hrs) | pH | % Growth (sedimentation values) | Zone Diameter (mm)* |
|---|---|---|---|
| 0 | 6.3 | — | — |
| 12 | 6.55 | 4.7 | — |
| 24 | 7.20 | 10.0 | 42 |
| 36 | 7.30 | 10.0 | 46 |
| 48 | 7.20 | 10.7 | 48 |
| 60 | 7.35 | 16.7 | 50 |
| 72 | 7.20 | 30.0 | 52.5 |
| 88 | 7.30 | 50.0 | 53.5 |
| 96 | 7.40 | 56.0 | 53.5 |
| 112 | 6.90 | 59.9 | 54.0 |
| 120 | 7.25 | 96.6 | 54.0 |

*Measured activity against *Streptococcus faecalis* 05045

Chemical Isolation of 2'-Chloropentostatin

A 680-liter portion of the harvested beer from Example 7 was adjusted to pH 6.5 and mixed with 31 kg of Celite 545 and filtered through a plate and frame filter press. The filtrate (680 liters) was mixed with 30 kg (4.4% w/v) Darco G-60 and, after the addition of 15.5 kg of Celite 545, filtered once more through a clean plate and frame filter press. The filter cake was washed with deionized water (185 liters), then eluted by circulating acetone-water (1:1, 151 liters) through the press three times. The acetone-water eluates, which contained most of the 2'-chloropentostatin, were combined and concentrated to 21 liters.

An eighteen-liter portion of the above 21 liter concentrate was stirred with 500 grams of Celite 545 and then filtered. Following the adjustment of pH from 6.5 to 5.1, the resulting filtrate (17 liters) was passed over ten liters of Dowex-50×2 resin (hydrogen form). After washing the resin with deionized water (19 liters), the column was eluted with 1N ammonium hydroxide (42 liters). The ammonium hydroxide eluate, which contained all of the 2'-chloropentostatin (as determined by HPLC assay), was concentrated to 400 milliliters and passed over 10 liters of Sephadex G-10. The column was eluted with deionized water, and nine 0.5-liter fractions and seven 1-liter fractions were collected. Most of the 2'-chloropentostatin was present in fractions fifteen and sixteen, each of which was concentrated to 200 ml and lyophilized to yield 6.3 g and 6.0 g, respectively, of amorphous solid. The 6.3 g of solid from fraction fifteen was treated with hot absolute ethanol (50 ml) affording 3.86 g of crystalline 2'-chloropentostatin upon cooling. Recrystallization from water (35 ml) yielded 2.9 g of colorless needles. Similar treatment of the 6.0 g of solid from fraction sixteen afforded 1.55 g of recrystallized 2'-chloropentostatin.

Properties of 2'-Chloropentostatin

Melting Point:
decomposition at approximately 180° C.

Ultraviolet Absorption Spectrum $\lambda_{max}$ ($\epsilon$), Methanol     284 nm (9380)
$\lambda_{max}$ ($\epsilon$), 0.05 M methanolic HCl     266 nm (8473)

Optical Rotation
$[\alpha]_D^{23}$ + 28.5° (1.26% in 0.1 M pH 7 phosphate buffer)

Elemental Analysis

| | % C | % H | % Cl | % N |
|---|---|---|---|---|
| Calcd. for $C_{11}H_{15}ClN_4O_4$ | 43.64 | 4.99 | 11.75 | 18.51 |
| Found | 43.83 | 4.96 | 11.76 | 18.62 |

Mass Spectrum (via fast atom bombardment)

Calcd. for $C_{11}H_{16}ClN_4O_4$ [M + H]     303.0860 m/z
Found     303.0868 m/z Infrared Absorption Spectra in KBr Principal absorptions at 3350, 1635, 1625, 1198, 1100, 1065, and 1048 reciprocal centimeters 360 MHz Proton Magnetic Resonance Spectrum in $D_2O$ Principal signals at:

(s = singlet, d = doublet, dd = doublet of doublets, m = multiplet) 3.26 m (2H), 3.65 m (2H), 4.11 m (1H), 4.33 dd (1H), 4.71 dd (1H), 4.98 d (1H), 5.87 d (1H), 7.01 s (1H), and 7.55 s (1H) parts per million downfield from sodium 2,2-dimethyl-2-silapentane-5-sulfonate (DSS).

90.4 MHz Carbon-13 Magnetic Resonance Spectrum in $D_2O$

Principal signals at:

| peak number | chemical shift* |
|---|---|
| 1 | 152.9 |
| 2 | 138.1 |
| 3 | 134.8 |
| 4 | 131.6 |
| 5 | 90.8 |
| 6 | 87.9 |
| 7 | 73.3 |
| 8 | 69.5 |
| 9 | 63.9 |
| 10 | 63.5 |
| 11 | 49.9 |

*parts per million downfield from tetramethylsilane

High Pressure Liquid Chromatography

| | |
|---|---|
| Column: | μBondapak ™ $C_{18}$ silica gel (3.9 mm I.D. × 30 cm) |
| Solvent: | 0.02 M pH 7.0 sodium phosphate buffer-acetonitrile (90:10) |
| Flow rate: | 1.0 ml/min |
| Detection: | ultraviolet absorption at 280 nm |
| Retention time: | 5.1 minutes |

Thin Layer Chromatography on Silica Gel 60 F254 (E. Merck)

| | |
|---|---|
| Solvent: | chloroform-ethanol-0.5 M sodium acetate pH 5.5 (40:70:20) |
| Detection: | iodine vapor |
| $R_f$: | 0.51 |

The compound of the invention forms pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, malonic, ascorbic, maleic, methanesulfonic and the like. The salts are prepared by contacting the free base form with an equivalent amount of the desired acid in the conventional manner. The free base form may be regenerated by treating the salt form with a base. For example, dilute aqueous base solutions may be utilized. Dilute aqueous sodium hydroxide, potassium carbonate, ammonia and sodium bicarbonate solutions are suitable for this purpose. The free base form differs from its respective salt form somewhat in certain physical properties such as solubility in polar solvents, but the salts are otherwise equivalent to the free base form for purposes of the invention.

Antimicrobial Activity

Paper disks (12.7 mm in diameter) impregnated with an aqueous solution containing varying amounts of 2'-chloropentostatin were placed on a layer of agar containing AM-10 assay medium (Table 4) and inoculated with *Streptococcus faecalis* 05045. After incubation at 37° overnight the following zones of inhibition were observed:

| Concentration | Zone diameter |
|---|---|
| 2000 μg/ml | 64 mm |
| 200 μg/ml | 61 mm |
| 20 μg/ml | 55 mm |
| 2 μg/ml | 47 mm |
| 0.2 μg/ml | 40 mm |

Adenosine Deaminase Activity of 2'-Chloropentostatin

The potency of 2'-chloropentostatin as an adenosine deaminase inhibitor was determined using the following methods. The velocity (in moles/minute/ml) of the reaction of adenosine deaminase with adenosine was measured for several concentrations of the enzyme in the presence of various concentrations of the inhibitor, 2'-chloropentostatin. The data has been plotted in FIG. 1 in the form of an Ackerman-Potter plot (see W. W. Ackerman and V. R. Potter, *Proc. Soc. Exp. Biol. Med.*, 72:1 (1949)). The fact that the traces, at higher concentrations of substrate, become parallel is indicative of the fact that 2'-chloropentostatin is a so-called "tight-binding" or "pseudo-irreversible" inhibitor of the enzyme, adenosine deaminase.

Figure 2:
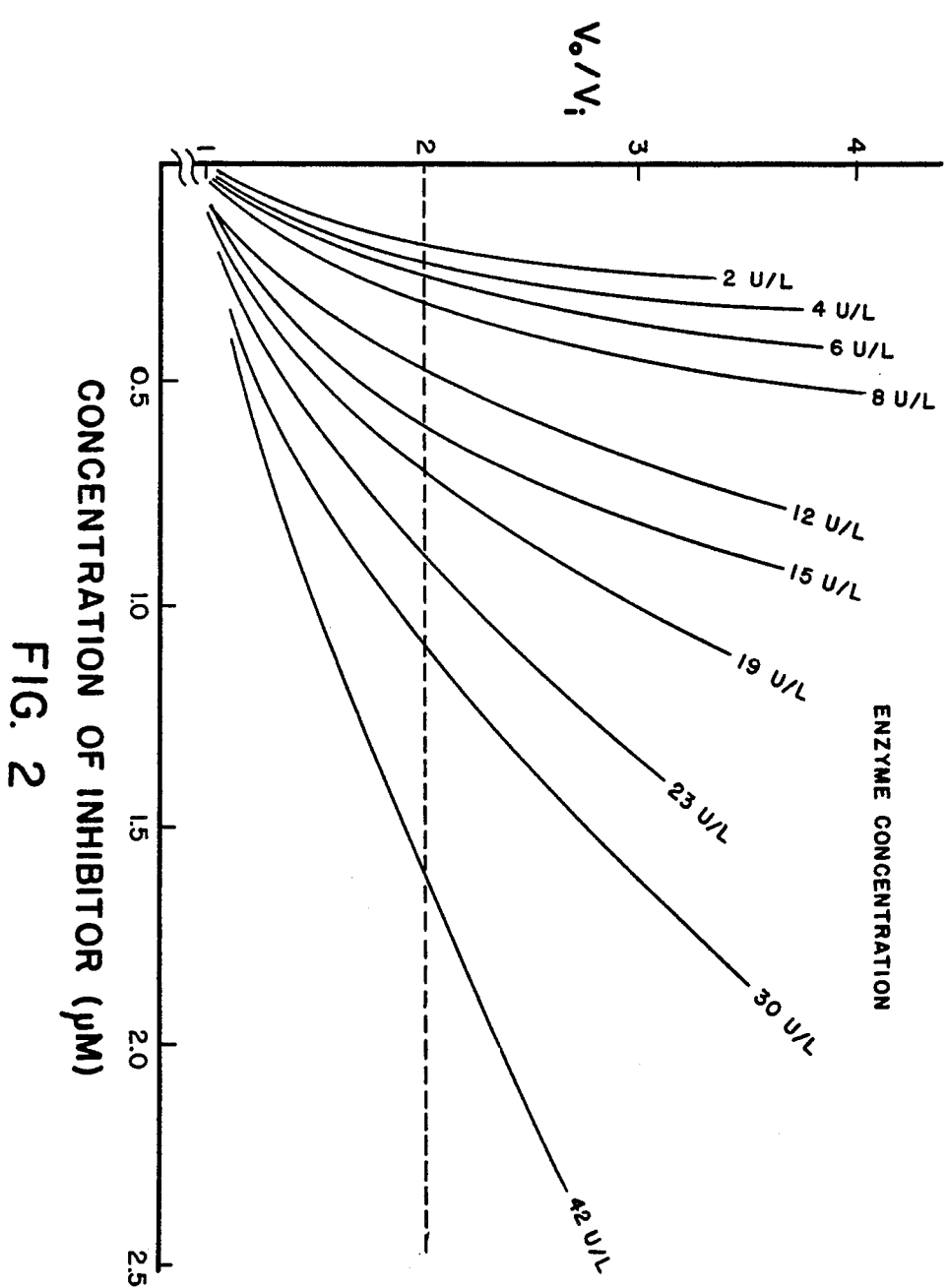
FIG. 2 is a plot of the ratio of velocities of uninhibited to inhibited reaction rates of adenosine with adenosine deaminase in the presence of 2'-chloropentostatin.
Figure 3:
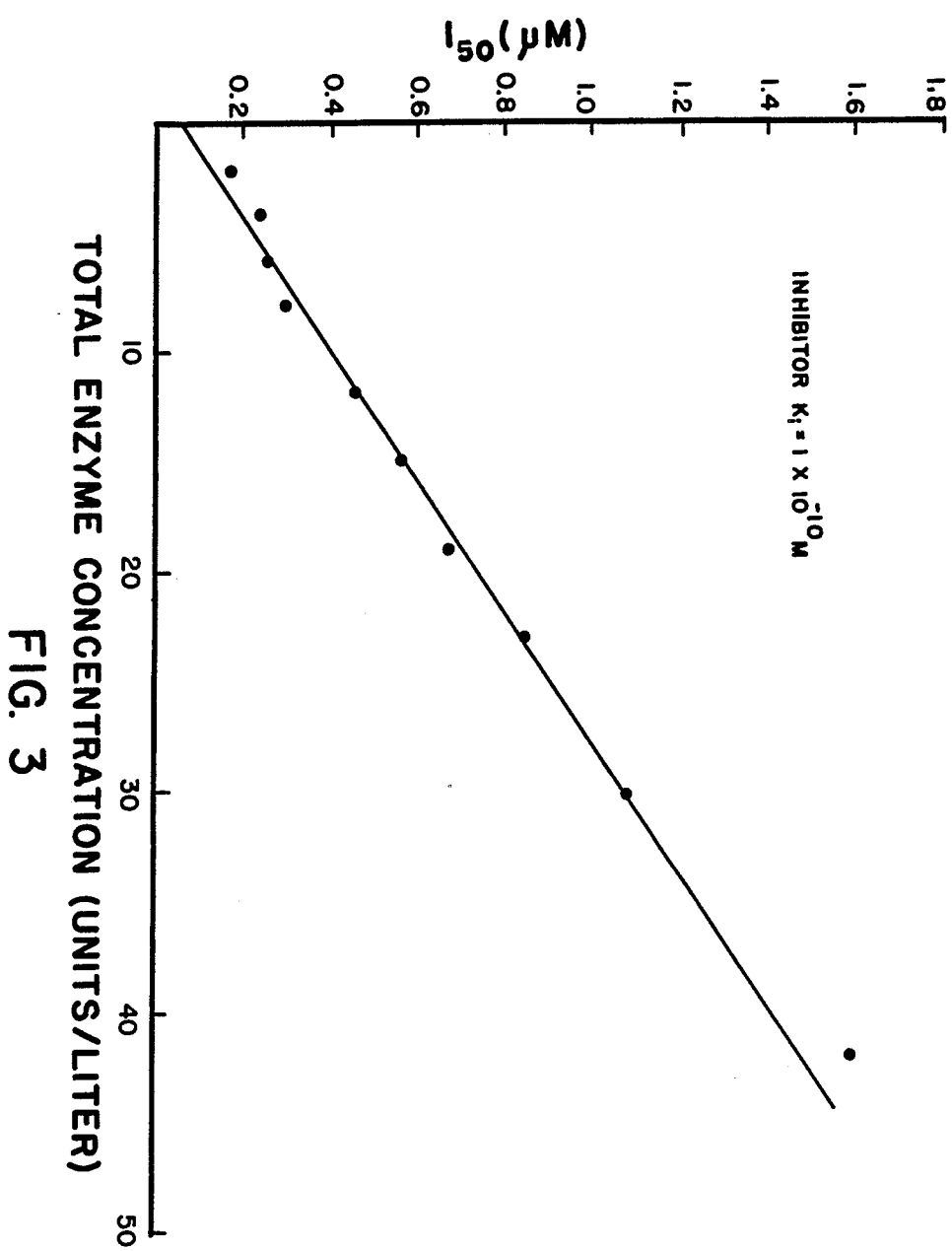
FIG. 3 is a plot of $I_{50}$ values of 2'-chloropentostatin inhibition of adenosine deaminase versus enzyme concentration.

In FIG. 2, the ratio of the velocity of the uninhibited reaction of adenosine with adenosine deaminase to the velocity of the same reaction in the presence of the inhibitor, 2'-chloropentostatin, has been plotted for several concentrations of substrate versus the micromolar concentrations of 2'-chloropentostatin. The values of $V_o/V_i = 2$ for each curve yield the $I_{50}$ for the enzyme inhibitor at each substrate concentration. These $I_{50}$ values have been plotted versus substrate concentration in FIG. 3. Extrapolation of the linear plot of FIG. 3 permits the determination of $K_i = 1 \times 10^{-10}$ molar for 2'-chloropentostatin.

The compound of the present invention, 2'-chloropentostatin is a very useful substance not only for the analysis of the causes of disease involving metabolism of adenosine and nucleic acids, but also as an agent for potentiating the activity of antiviral agents which contain an adenine moiety such as the substance 9-(beta-D-arabinofuranosyl)adenine. The latter substance is disclosed in U.S. Pat. No. 3,616,208 (incorporated herein by reference) as a useful agent for the treatment of DNA viruses, especially herpes and vaccinia viruses in mammals. The biological efficacy of adenine-derived antiviral agents such as 9- (beta-D-arabinofuranosyl)adenine, is greatly diminished by the rapid deamination of such materials in vivo by the enzyme, adenosine deaminase.

2'-Chloropentostatin is administered in conjunction with adenine-derived antiviral agents to potentiate the activity of the latter by inhibiting adenosine deaminase enzymes. In a preferred embodiment, 2'-chloropentostatin is combined in a pharmaceutical composition with the antiviral agent 9-(beta-D-arabinofuranosyl)adenine.

More particularly, 2'-chloropentostatin is administered in combination with an adenine-derived antiviral agent in ratios of from about 0.005 to about 0.5 parts of 2'-chloropentostatin to about 1 part of the antiviral agent. The preferred range is from 0.01 to 0.25 parts of 2'-chloropentostatin to 1 part of the antiviral agent. In the particular case where 2'-chloropentostatin is administered together with 9-(beta-D-arabinofuranosyl)adenine, the preferred range is from 0.01 to 0.25 parts of the compound of this invention to 1 part of 9-(beta-D-arabinofuranosyl)adenine. More specifically, when the composition is administered parenterally, preferably intravenously, injectable solutions are given so as to provide the host with from 0.1 mg to 5.0 mg of 9-(beta-D-arabinofuranosyl)adenine per kg of body weight and 0.0005 mg to 0.1 mg of the compound of this invention per kg of body weight per day. The preferred quantity which is administered on a daily basis is from about 0.5 mg to 5.0 mg of 9-(beta-D-arabinofuranosyl)adenine per kg of body weight to about 0.005 mg to 0.02 mg of the compound of this invention per kg of body weight.

The pharmaceutical composition may be in bulk form containing 0.005 to 0.5 parts of the compound of this invention to about 1 part of 9-(beta-D-arabinofuranosyl)adenine which is placed in solution at time of use by the addition of a solvent which is appropriate for injectables. In the alternative, the pharmaceutical composition may be an aqueous solution containing a ratio of from 0.005 to 0.5 parts of the compound of this invention to about 1 part of 9-(beta-D-arabinofuranosyl)adenine and other materials such as preservatives, buffering agents, agents intended to adjust the isotonicity of the solution, etc. The volume of water is not critical and may vary from less than 1 ml to about 500 ml.

We claim:

1. The compound 2'chloropentostatin having adenosine deaminase inhibitory activity and possessing the structure

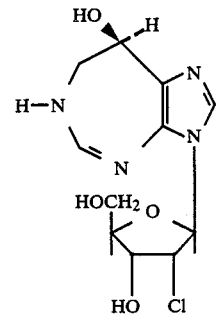

or a pharmaceutically acceptable acid addition salt thereof.

2. A pharmaceutical composition useful for the treatment of DNA viruses comprising from 0.005 to 0.5 parts of 2'-chloro- pentostatin or a pharmaceutically acceptable acid addition salt thereof in combination with 1 part of 9-($\beta$-D-arabinofuranosyl)adenine and a pharmaceutically acceptable carrier.

3. A method of treating infections of DNA viruses in a mammal comprising administering to a mammal in need of such treatment an effective amount of a pharmaceutical composition in accordance with claim 2.

* * * * *